(12) United States Patent
Khouri et al.

(10) Patent No.: US 7,981,996 B2
(45) Date of Patent: Jul. 19, 2011

(54) METHOD OF MAKING BISIMIDES

(75) Inventors: Farid Fouad Khouri, Niskayuna, NY (US); Albert Santo Stella, Voorheesville, NY (US)

(73) Assignee: Sabic Innovative Plastics IP B.V. (NL)

( * ) Notice: Subject to any disclaimer, the term of this patent is extended or adjusted under 35 U.S.C. 154(b) by 0 days.

(21) Appl. No.: 11/600,538

(22) Filed: Nov. 16, 2006

(65) Prior Publication Data

US 2008/0119660 A1 May 22, 2008

Related U.S. Application Data

(63) Continuation-in-part of application No. 11/232,285, filed on Sep. 21, 2005, which is a continuation-in-part of application No. 11/022,907, filed on Dec. 22, 2004.

(51) Int. Cl.
*C08G 8/02* (2006.01)

(52) U.S. Cl. .......... 528/125; 528/26; 528/126; 528/128; 528/170; 528/171; 528/353; 528/425

(58) Field of Classification Search ................. 528/125, 528/126, 128, 170–175, 182, 185, 188, 220, 528/353

See application file for complete search history.

(56) References Cited

U.S. PATENT DOCUMENTS

| | | | |
|---|---|---|---|
| 3,787,364 A | 1/1974 | Wirth et al. | |
| 5,182,392 A | 1/1993 | Tanisake et al. | |
| 5,229,482 A | 7/1993 | Brunelle | |
| 5,817,425 A | 10/1998 | Morishige et al. | |
| 5,830,974 A | 11/1998 | Schmidhauser et al. | |
| 6,235,866 B1 * | 5/2001 | Khouri et al. | 528/125 |
| 6,248,879 B1 | 6/2001 | Anderson et al. | |
| 2006/0135741 A1 | 6/2006 | Gui et al. | |

FOREIGN PATENT DOCUMENTS

| | | |
|---|---|---|
| EP | 0 892 003 | 1/1999 |
| WO | WO 01/25196 | 4/2001 |
| WO | WO 2005/023903 | 3/2005 |

OTHER PUBLICATIONS

"Specification on 4-Chlorophatalic Anhydride" Jiansu tianyin Chemical Industry.*
Guggenheim et al., U.S. Appl. No. 11/095,200, filed Mar. 30, 2005, "Method for Preparation of Salts of Hydroxy-Substituted Aromatic Compounds", GE Docket No. 145827-1.

* cited by examiner

*Primary Examiner* — James Seidleck
*Assistant Examiner* — Gregory Listvoyb
(74) *Attorney, Agent, or Firm* — Cantor Colburn LLP; Diderico van Eyl (57) ABSTRACT

The present invention provides a method for preparing relatively insoluble bisimides under conditions which afford high imidization reaction rates and which permit the monitoring and adjustment of reactant stoichiometry at any stage of the reaction. The bisimides provided by the present invention are prepared either by reaction of a diamine such as 4,4'-diaminodiphenylsulfone (DDS) with an anhydride, for example 3-chlorophthalic anhydride (3-ClPA) in the presence of a solvent at a pressure greater than one atmosphere and at a temperature above the normal boiling point of the solvent, or by reaction of a monoamine with a dianhydride under the same conditions. In one embodiment, the relatively insoluble product bisimides provided by the present invention have a solubility in ortho-dichlorobenzene of less than about 10 percent by weight at a temperature of about 180° C.

12 Claims, 1 Drawing Sheet

FIG. 1

METHOD OF MAKING BISIMIDES

This application is a Continuation-In-Part of Patent Application No. US 2006/0135731 entitled "Method For The Preparation Of Bis(Haloimides)", filed Sep. 21, 2005, which is a Continuation-In-Part of Patent Application No. US 2006/0135741 entitled "Method To Prepare Bis(Haloimides)", filed 22 Dec. 2004, both of which are incorporated by reference herein.

BACKGROUND

In one aspect this invention relates to a method of making bisimides having limited solubility in organic solvents. In another aspect, this invention relates to an improved method for the preparation of bis(halophthalimides) monomers useful for the preparation of polyetherimides.

Various types of polyether polymers, such as polyetherimides, polyethersulfones, polyetherketones, and polyetherketones, have become important as engineering resins by reason of their excellent properties. These polymers are typically prepared by the reaction of dihydroxyaromatic compounds, such as bisphenol A disodium salt, with dihaloaromatic compounds. For example, polyetherimides are conveniently prepared by the reaction of salts of dihydroxyaromatic compounds with bis(halophthalimides).

U.S. Pat. Nos. 5,229,482 and 5,830,974, disclose the preparation of aromatic polyether polymers in relatively non-polar solvents, using a phase transfer catalyst which is substantially stable under the polymerization conditions. Solvents disclosed in U.S. Pat. No. 5,229,482 include o-dichlorobenzene, dichlorotoluene, 1,2,4-trichlorobenzene and diphenyl sulfone. U.S. Pat. No. 5,830,974 discloses the use of solvents such as anisole, diphenylether, and phenetole. Solvents of the same type may be used for the preparation of bis(halophthalimide) intermediates for polyetherimides.

In each of U.S. Pat. Nos. 5,229,482 and 5,830,974 the bis(halophthalimide) is introduced into the polymerization reaction as a substantially pure, isolated compound. This process step is often difficult, since solid bis(halophthalimides) are typically of very low density and fluffy, making weighing and handling burdensome. By contrast, U.S. Pat. No. 6,235,866 discloses the preparation of a slurry comprising a bis(halophthalimide). The slurry comprising the bis(halophthalimide) is prepared by reacting roughly equimolar quantities of a diamine and a halophthalic anhydride in a solvent to produce the product bis(halophthalimide) and water as a by-product. The slurry comprising the bis(halophthlimide) must be rigorously dried prior to reaction with, for example, bisphenol A disodium salt, to form a product polyetherimide. Producing a dry slurry of the bis(halophthalimide) in a solvent, for example a slurry of bis(4-chlorophthalimide) in ODCB containing less than about 10 ppm water, presents significant challenges. The reaction between the diamine and the halophthalimide is typically dried by distilling a large volume of solvent from the reaction mixture which entrains the by-product water out of the reaction mixture. This method of water removal, although effective as a means of drying the reaction mixture, is inefficient since a relatively large volume of solvent must be distilled from the reaction mixture in order to remove a relatively small amount of water. Reactions wherein by-product water is removed by distillation are characterized by long reaction times, high reaction temperatures, and the use of large volumes of solvent. Under such circumstances, the product bis(halophthalimide) is subject to an increased likelihood of degradation, and the overall process is rendered inefficient as a result of the time and expense required to distill large volumes of solvent. Further, if the diamine has a significant vapor pressure at the imidization reaction temperature (such as m-phenylene diamine), then some of the diamine may be distilled along with the solvent and water byproduct, thus upsetting the reaction stoichiometry and requiring wastewater cleanup. Moreover, when the product bis(halophthalimide) is relatively insoluble the reaction between the diamine and the halophthalic anhydride is characterized by thick phase behavior in which the reaction mixture becomes highly heterogeneous and cannot be agitated effectively. Thick phase behavior is implicated in a variety of undesirable outcomes, such as low reaction rates and low product qualities. The avoidance of thick phase behavior during the preparation of bis(halophthalimides) in particular, and bisimides generally is thus highly desirable.

Thus, there is a need in the art to develop a facile process for the preparation of bis(halophthalimides) having suitable characteristics for conversion to polyetherimide polymers without isolation that overcomes the shortcomings of current synthetic methods. There is also a need to develop processes for the preparation of relatively insoluble bisimdes, such as bis(halophthalimides), which avoids reaction conditions exhibiting thick phase behavior.

BRIEF DESCRIPTION

In one embodiment, the present invention provides a method for making a bisimide, the method comprising:
(a) adding a molten first reactant to a mixture comprising a solvent and a second reactant to provide a uniform reaction mixture;
(b) agitating the uniform reaction mixture while removing water formed in an imidization reaction to afford a uniform product mixture comprising a product bisimide, the product bisimide being present in an amount corresponding to at least 20 percent solids, the product bisimide having a solubility in ortho-dichlorobenzene of less than about 10 percent by weight at a temperature of about 180° C.;

said adding and said agitating being carried out at a temperature greater than the boiling point of the solvent at a pressure greater than 1 atmosphere.

In another embodiment, a method for making a bisimide, the method comprising:
(a) adding a molten haloaromatic anhydride to a mixture comprising a solvent and an aromatic diamine to provide a uniform reaction mixture;
(b) agitating the uniform reaction mixture while removing water formed formed in an imidization reaction to afford a uniform product mixture comprising a product bisimide, the product bisimide being present in an amount corresponding to at least 20 percent solids, the product bisimide having a solubility in ortho-dichlorobenzene of less than about 10 percent by weight at a temperature of about 180° C.;

said adding and said agitating being carried out at a temperature greater than the boiling point of the solvent at a pressure greater than 1 atmosphere.

In yet another embodiment, the present invention provides a method for making a bisimide, the method comprising:
(a) adding molten chlorophthalic anhydride to a mixture comprising ODCB solvent and 4,4'-diaminodiphenylsulfone to provide a uniform reaction mixture;
(b) agitating the uniform reaction mixture while removing water formed in an imidization reaction to afford a uniform product mixture comprising a product bisimide, the product bisimide being present in an amount corresponding to at least 20 percent solids, the product bisimide having a solubility in ortho-dichlorobenzene of less than about 10 percent by weight at a temperature of about 180° C.;

said adding and said agitating being carried out at a temperature greater than the boiling point of the ODCB solvent at a pressure greater than 1 atmosphere.

These and other features, aspects, and advantages of the present invention may be more understood more readily by reference to the following detailed description.

BRIEF DESCRIPTION OF DRAWINGS

Various features, aspects, and advantages of the present invention will become better understood when the following detailed description is read with reference to the accompanying drawing.

DETAILED DESCRIPTION

In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO-), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —O C$_6$HR$_{10}$(CH$_2$)$_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$C$_6$H$_{10}$—), 4-vinylcyclohexen-1-yl, vinylidenebis(cyclohexyl), and the like. The term "a C$_3$-C$_{10}$ cycloaliphatic radical" includes cycloaliphatic radicals containing at least three but no more than 10 carbon atoms. The cycloaliphatic radical 2-tetrahydrofuranyl (C$_4$H$_7$O—) represents a C$_4$ cycloaliphatic radical. The cyclohexylmethyl radical (C$_6$H$_{11}$CH$_2$—) represents a C$_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a C$_6$ aliphatic radical comprising a methyl group, the methyl group being a functional group which is an alkyl group. Similarly, the 4-nitrobut-1-yl group is a C$_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e., —CHO), hexyl, hexamethylene, hydroxymethyl (i.e., —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilylpropyl (i.e., (CH$_3$O)$_3$SiCH$_2$CH$_2$CH$_2$—), vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical.

As noted above, one aspect of the present invention is a method for making a bisimide. The method comprises adding a molten first reactant to a mixture comprising a solvent and a second reactant at a temperature greater than the boiling point of the solvent at a pressure greater than 1 atmosphere to provide a uniform reaction mixture. The uniform reaction mixture is then agitated at a temperature greater than the boiling point of the solvent at a pressure greater than 1 atmosphere while removing water formed in an imidization reaction to afford a uniform product mixture comprising a product bisimide. The product bisimide is present in the uniform product mixture in an amount corresponding to at least 20 percent solids. In one embodiment, the product bisimide is present in the uniform product mixture in an amount corresponding to at least 25 percent solids. In yet another embodiment, the product bisimide is present in the uniform product mixture in an amount corresponding to at least 30 percent solids. The product bisimides provided by the method of the present invention are relatively insoluble. In one embodiment, the product bisimide has solubility in ODCB of less than about 10 percent by weight at a temperature of about 180° C. In another embodiment, the product bisimide has a solubility in ODCB of less than about 5 percent by weight at a temperature of about 180° C. In yet another embodiment, the product bisimide has a solubility in ODCB of less than about 2 percent by weight at a temperature of about 180° C. Both the uniform reaction mixture and the uniform product mixture are characterized by relatively low viscosities, meaning that the uniform reaction mixture and the uniform product mixture are readily stirrable.

In one embodiment of the present invention, the first reactant is a diamine. In one embodiment, the diamine is a diamino aromatic compound which may be represented by formula (I)

$$H_2N—B—NH_2 \qquad (I)$$

wherein B is a C$_3$-C$_{30}$ divalent aromatic radical. In one embodiment B is a monocyclic divalent aromatic radical, for example paraphenylene, metaphenylene, or orthophenylene. In an alternate embodiment B is a polycyclic divalent aromatic radical, for example 4,4'-biphenylene or 1,4-naphthalene.

In one embodiment B is a C$_3$-C$_{30}$ divalent aromatic radical having structure (II)

wherein the unassigned positional isomer about the aromatic ring is either ortho, meta or para to Q, and Q is a linking group chosen from a covalent bond, an alkylene group of the formula C$_y$H$_{2y}$, or an alkylidene group of the formula C$_y$H$_{2y}$; wherein "y" is an integer from 1 to 5 inclusive. In some particular embodiments "y" has a value of one or two. Illustrative alkylene and alkylidene linking groups Q include, but are not limited to, methylene, ethylene, ethylidene, propylene, and isopropylidene. In other particular embodiments, the unassigned positional isomer about the aromatic ring in formula (II) is para to Q.

Diamino aromatic compounds (I) are illustrated by meta-phenylenediamine, para-phenylenediamine, 2-chloro-1,3-diaminobenzene; 2-methyl-1,3-diaminobenzene; 2,6-dichloro-1,4-diaminobenzene; 2,6-dimethyl-1,4-diaminobenzene; 2,3,5,6-tetrachloro-1,4-diaminobenzene; 2,2-bis(4-aminophenyl)propane; bis(2-chloro-4-amino-3,5-diethylphenyl) methane; 4,4'-diaminobiphenyl; 3,4'-diaminobiphenyl; 3,3'-diaminobiphenyl; 3,3'-dichloro-4,4'-diaminobiphenyl; 3,3'-dimethoxy-4,4'-diaminobiphenyl; 2,2',6,6'-tetramethyl-4,4'-diaminobiphenyl; 3,3'-dimethoxy-4,4'-diaminobiphenyl; 4,4'-diaminodiphenylmethane; 3,3'-diaminodiphenylmethane; 1,3-bis(3-aminophenoxy)benzene; 1,3-bis(4-aminophenoxy)benzene; 1,4-bis(4-aminophenoxybenzene); bis (4-(4-aminophenoxy)phenyl)sulfone; bis(4-(3-aminophenoxy)phenyl)sulfone; 4-(4-aminophenoxy)phenyl) (4-(3-aminophenoxy)phenyl)sulfone; 4,4'-bis(3-aminophenoxy)biphenyl; 4,4'-bis(4-aminophenoxy) biphenyl; 4-(3-aminophenoxy)-4'-(4-aminophenoxy) biphenyl; 2,2'-bis(4-(4-aminophenoxy)phenyl)propane; 2,2-bis[4-(4-aminophenoxy)phenyl]hexafluoropropane; and 4,4'-(9-fluorenylidene)dianiline;

Diamino aromatic compounds comprising structure II are illustrated by 3,4'-diaminodiphenylmethane; 2,2-bis(4-aminophenyl)hexafluoropropane; 4,4'-diaminodiphenyl ether; 3,4'-diaminodiphenyl ether; 3,3'-diaminodiphenyl ether; 4,4'-diaminodiphenylsulfide; 4,4'-diaminodiphenylsulfoxide, 3,3'-diaminodiphenylsulfide; 3,3'-diaminodiphenylsulfone; 4,4'-diaminodiphenylsulfone (DDS); 3,4'-diaminodiphenylsulfone; 4,4'-diaminodiphenylketone; 3,4'-diaminodiphenylketone; and 3,3'-diaminodiphenylketone.

In one embodiment the diamine is selected from the group consisting of ortho-phenylenediamine, meta-phenylenediamine, para-phenylenediamine, 4,4'-oxydianiline, 4,4'-diaminiodiphenylsulfone, and combinations of the foregoing aromatic diamines. In another embodiment, the diamine is 4,4'-diaminodiphenylsulfone (DDS).

In one embodiment, the first reactant is a diamine which comprises at least two diamino aromatic compounds. For example, the ETHACURE diamines, available from Albemarle Corporation, Baton Rouge, La., such as ETHACURE 100, which is a 80:20 weight ratio combination of 2,6-diethyl-4-methyl-1,3-phenylene diamine and 4,6-diethyl-2-methyl-1,3-phenylene diamine, respectively; and ETHACURE 300 which is a 80:20 weight ratio combination of 2,6-bis(mercaptomethyl)-4-methyl-1,3-phenylenediamine and 4,6-bis(mercaptomethyl)-2-methyl-1,3-phenylene diamine, respectively, may also be used. Perfluorinated alkyl or partially fluorinated alkyl analogs of said diamines are also suitable for use.

In an alternate embodiment of the present invention, the second reactant is a diamine. In embodiments wherein the second reactant is a diamine, it may be any of the various diamines disclosed herein. In a particular embodiment, the second reactant is the diamine 4,4'-diaminodiphenyl sulfone sometimes referred to herein as DDS. In an alternate embodiment, the second reactant comprises a mixture comprising at least two diamino aromatic compounds, for example a mixture of meta-phenylenediamine and para-phenylenediamine.

In one embodiment of the present invention, the first reactant is an anhydride. In another embodiment, the anhydride is a haloaromatic anhydride. In yet another embodiment the anhydride is a halophthalic anhydride represented by generic structure (III)

wherein X is a fluorine, chlorine, bromine, or iodine atom. Suitable halophthalic anhydrides are illustrated by 3-fluorophthalic anhydride (3-FPA), 4-fluorophthalic anhydride (4-FPA), 3-chorophthalic anhydride (3-ClPA), 4-chorophthalic anhydride (4-ClPA), 3-bromophthalic anhydride (3-BrPA), 4-bromophthalic anhydride (4-BrPA), 3-iodophthalic anhydride (3-IPA), and 4-iodophthalic anhydride (4-IPA).

Other anhydrides are also suitable for use according to the method of the present invention. Thus, in one embodiment, the second reactant is an anhydride which is not a halophthalic anhydride. For example, in one embodiment, the second reactant may be any one of phthalic anhydride itself, 3-nitrophthalic anhydride, 4-nitrophthalic anhydride, and 4-cyanoophthalic anhydride, or a mixture comprising two or more of the foregoing.

Other anhydrides which are not halophthalic anhydrides are also suitable, for example 6-F dianhydride, benzophenone dianhydride, BPA dianhydride, and 3,4-biphenyl dianhydride. Those skilled in the art will appreciate that a bisimide may be formed from a dianhydride upon reaction of the dianhydride with a monomamine. Thus, in one embodiment, the present invention provides a method for the preparation of bisimides involving the reaction of a dianhydride with a monoamine. Suitable monoamines include aniline, 4-nitroaniline, 4-carboxyaniline and the like.

In various embodiments, a high degree of purity is required in the anhydride to achieve a suitable level of purity in the product bisimide. For example, halophthalic anhydrides having a high degree of purity are required for various applications. In one embodiment, the first reactant is a halophthalic anhydride selected from the group consisting of 3-ClPA, 4-ClPA, and mixtures thereof. Impurities which may be present in 3-ClPA, 4-ClPA, and mixtures thereof (collectively ClPA) include the isomeric halobenzoic acids (IV), and the isomeric halophthalides (V)

wherein X is a fluorine, chlorine, bromine, or iodine atom. In one embodiment of the present invention, halophthalic anhydride products contain less than about 10,000 parts per million of halophthalide (all halophthalide isomers), preferably less than about 1000 parts per million of halophthalide, and more preferably less than about 500 parts per million of halophthalide. Additionally, halophthalic anhydride containing less than about 1 percent by weight of phthalic anhydride. In certain instances, phthalic anhydride may be present as an impurity in the halophthalic anhydride employed. This is particularly true where the halophthalic anhydride has been prepared by catalytic oxidation of the corresponding halo-orthoxylene. Phthalic anhydride may arise by dehalogenation during the catalytic oxidation of 4-chloro-orthoxylene by oxygen in the presence of cobaltous acetate, manganous acetate, and hydrogen bromide, in acetic acid solvent at elevated temperature and pressure.

As noted, in one embodiment, the anhydride can be a dianhydride, for example a dianhydrides represented by structure (VI)

wherein $R^1$ is a halogen atom, a nitro group, a $C_1$-$C_{12}$ aliphatic radical, $C_3$-$C_{12}$ cycloaliphatic radical, or a $C_3$-$C_{12}$ aromatic radical; b is independently at each occurrence 0 or an integer from 1 to 3; W is a bond, an oxygen atom, a sulfur atom, a sulfinyl group, a sulfonyl group, a selenium atom, a hexafluoroisopropylidene group, a $C_1$-$C_{30}$ aliphatic radical, a $C_3$-$C_{30}$ cycloaliphatic radical, or a $C_3$-$C_{30}$ aromatic radical, or a carbonyl group. In one embodiment, W is a linking group having structure (VII)

wherein each $G^1$ is independently an $C_3$-$C_{20}$ aromatic radical; E is selected from the group consisting of a $C_3$-$C_{20}$ cycloaliphatic radical, a $C_3$-$C_{20}$ aromatic radical, a $C_1$-$C_{20}$ aliphatic radical, a sulfur-containing linkage, a phosphorus-containing linkage, an ether linkage, a carbonyl group, a tertiary nitrogen atom, and a silicon-containing linkage; $R^2$ is independently at each occurrence a halogen atom, a $C_1$-$C_{20}$ aliphatic radical, $C_3$-$C_{20}$ cycloaliphatic radical, or a $C_3$-$C_{20}$ aromatic radical; $Y^1$ is independently at each occurrence a halogen atom, a nitro group, a cyano group, a $C_1$-$C_{20}$ aliphatic radical, $C_3$-$C_{20}$ cycloaliphatic radical, or a $C_3$-$C_{20}$ aromatic radical; each m is independently a number from zero through the number of positions on each respective $G^1$ available for substitution; p is a whole number from zero through the number of positions on E available for substitution; t is a number greater than or equal to one; s is either zero or one; and u is a whole number including zero. Suitable dianhydrides represented by formula (VI) are illustrated by 4,4'-biphenol diphthalic anhydride; 4,4'-oxydiphthalic anhydride; 4,4'-thiodiphthalic anhydride; sulfinyldiphthalic anhydride; sulfonyldiphthalic anhydride; 4,4'-selenyldiphthalic anhydride; 4,4'-(hexafluoroisiopropylidene)diphthalic anhydride (CAS No. 1102-00-2); 4,4'-carbonyldiphthalic anhydride (CAS No. 2421-28-5); and 4,4'-(4,4'-isopropylidene diphenoxy)bis(phthalic anhydride) i.e. bisphenol A bisphthalic anhydride sometimes referred to herein as BPADA.

In a specific embodiment of the present invention, the dianhydride used is 4,4'-oxydiphthalic anhydride (hereinafter sometimes referred to as "ODPA") (structure VIII). In an alternate embodiment, the dianhydride is BPADA (structure IX). In alternate embodiments, minor amounts of the 3,3'-oxydiphthalic anhydride and 3,4'-oxydiphthalic anhydride may be present along with the 4,4'-oxydiphthalic anhydride.

In one embodiment, the dianhydride is selected from the group consisting of 3,3'-oxydiphthalic anhydride and 3,4'-oxydiphthalic anhydride.

The dianhydrides VIII and IX are commercially available or may be prepared by methods known to those skilled in the art. The dianhydride, 4,4'-oxydiphthalic anhydride (structure VIII, CAS No. 1823-59-2) (ODPA) is a preferred dianhydride for some applications and is available commercially from Aldrich Chemical Co. The dianhydride, BPADA (structure IX, CAS #38103-06-9) is a preferred dianhydride for some applications and is available commercially from Aldrich Chemical Co.

In an alternate embodiment of the present invention, the second reactant is an anhydride. In embodiments wherein the second reactant is an anhydride, it may be any of the various anhydrides disclosed herein. In one embodiment, the second reactant is a halophthalic anhydride. In a particular embodiment, the second reactant is a halophthalic anhydride selected from the group consisting of 3-chlorophthalic anhydride, 4-chlorophthalic anhydride, and mixtures thereof. In one embodiment, the second reactant is a halophthalic anhydride consisting essentially of 3-chlorophthalic anhydride. In an alternate embodiment, the second reactant is a halophthalic anhydride consisting essentially of 4-chlorophthalic anhydride. In yet another embodiment, the second reactant is a halophthalic anhydride consisting essentially of 3-chlorophthalic anhydride and 4-chlorophthalic anhydride. In one embodiment, the second reactant comprises at least two different anhydrides, for example a 1 to 1 mixture of 3-fluorophthalic anhydride and 4-fluorophthalic anhydride.

The method of the present invention comprises the addition of a molten first reactant to a mixture comprising a solvent and a second reactant to provide a uniform reaction mixture. Suitable solvents include non-polar solvents and polar aprotic solvents. Typically, an aromatic solvent is employed, for example an aromatic hydrocarbon solvent or chloroaromatic solvent. In one embodiment, the solvent has a boiling point above about 120° C., preferably above about 150° C., and more preferably above about 180° C. at atmospheric pressure.

Suitable solvents are exemplified by, but are not limited to, toluene, xylene, ortho-dichlorobenzene (ODCB), para-dichlorobenzene, chlorobenzene, dichlorotoluene; 1,2,4-trichlorobenzene; diphenylether, dimethylsulfone, diphenyl sulfone, sulfolane, phenetole, anisole, mesitylene, ortho cresol (o-cresol), veratrole, and mixtures thereof. In a preferred embodiment, chlorinated aromatic solvents are employed as solvents, examples of which include, but are not limited to, ortho-dichlorobenzene (ODCB); 2,4-dichlorotoluene; and 1,2,4-trichlorobenzene.

In the various embodiments of the present invention, the solvent may be selected to permit the attainment of relatively high temperatures without generating high internal reactor pressure. Thus, in some embodiments 2,4-dichlorotoluene and ODCB are preferred solvents so that relatively high temperatures can be achieved at relatively low pressures. As noted earlier in this disclosure, in various embodiments the method of the present invention employs temperatures in excess of the boiling point of the solvent and pressures above 1 atmosphere. Higher boiling solvents permit the attainment of higher reaction rates at relatively modest superatmospheric pressures.

In certain embodiments, water formed during the imidization reaction taking place between the first reactant and the second reactant is removed during the addition of the first reactant to the mixture comprising the solvent and the second reactant. This concurrent water removal results from the fact that the addition of the first reactant to the mixture comprising a solvent and a second reactant is carried out at a temperature which is in excess of the boiling point of the solvent at ambient pressure, and further the temperature is in excess of the boiling point of water under the reaction conditions. In a typical embodiment, the temperature is above the boiling point of water under the reaction conditions but below the boiling point of the solvent under the reaction conditions. In many instances, the water and solvent together form an azeotrope which distills from the reaction mixture at a temperature above the boiling point of water under the reaction conditions but below the boiling point of the solvent under the reaction conditions. In various embodiments, the method of the present invention employs a partial condenser to condense a portion of the solvent present in an azeotropic mixture while minimizing the co-condensation of water. Those skilled in the art will understand that a partial condenser may be operated at a temperature which is above the boiling point of water under the reaction conditions but which temperature is below the boiling point of the solvent under the reaction conditions. Under such circumstances, water may be removed from the reaction mixture more efficiently than might otherwise be possible since solvent is continuously returned to the reaction mixture as water is removed.

In one embodiment, the method of the present invention comprises adding a molten first reactant to a mixture comprising the solvent and the second reactant to provide a uniform reaction mixture, said reaction being carried out at a temperature greater than the normal boiling point of the solvent, said adding being carried out at a pressure greater than 1 atmosphere. The uniform reaction mixture is then agitated (e.g. stirred) while the imidization reaction takes place and water formed in the imidization reaction is distilled out of the reaction mixture. There is provided thereby a uniform product mixture comprising the product bisimide. It will be understood by those skilled in the art that the word "mixture" as used herein refers to a combination of at least two components. In one embodiment, the mixture is a slurry, i.e. a combination of a solvent and at least one other component, the combination comprising a solid or solids suspended in the solvent. In an alternate embodiment, a mixture may be a homogeneous solution. As used herein the term "uniform" refers to a mixture comprising "n" 1 cc volume elements, wherein the composition in the first volume element is the same as that of the "$n^{th}$" volume element. Thus, while a uniform reaction mixture may be a slurry or a homogeneous solution, it is characterized by compositional uniformity throughout. A uniform reaction mixture which is a slurry must be agitated to achieve compositional uniformity of the first and $n^{th}$ volume elements, and the compositional uniformity of the first and $n^{th}$ volume elements must be achievable by agitation. In the comparative examples shown herein, heterogeneous reaction mixtures exhibiting "thick phase" behavior are illustrated. Heterogeneous reaction mixtures are said to exhibit thick phase behavior because compositional uniformity cannot be achieved by agitation, i.e. the components of the mixture cannot be mixed effectively by stirring or other means. In one embodiment, the uniform reaction mixture is a homogeneous solution.

The uniform product mixture may be a slurry or a homogeneous solution. When the uniform product mixture product mixture is a slurry, it must be agitated to achieve compositional uniformity. In one embodiment, the uniform reaction mixture is a slurry and the uniform product mixture is a homogeneous solution. In an alternate embodiment, both the uniform reaction mixture and the uniform product mixture are slurries. In yet another embodiment, the uniform reaction mixture is a homogeneous solution and the uniform product mixture is a slurry. In yet another embodiment, both the uniform reaction mixture and the uniform product mixture are homogeneous solutions.

As noted, in one embodiment, the temperature at which the uniform reaction mixture is formed is greater than the boiling point of the solvent employed, and the pressure at which the uniform reaction mixture is formed is greater than one atmosphere. In one embodiment, the temperature at which the uniform reaction mixture is formed is greater than about 120° C. In an alternate embodiment, the temperature at which the uniform reaction mixture is formed is greater than about 150° C. In yet another embodiment, the temperature at which the uniform reaction mixture is formed is greater than about 180° C. In one embodiment, the temperature at which the uniform reaction mixture is formed is in a range from about 180 to about 250° C., and in an alternate embodiment, in a range from about 210 to about 230° C.

The phrase "agitating the uniform reaction mixture" refers to any process by which the uniform reaction mixture may be agitated, for example by stirring, shaking, or tumbling. As noted, in one embodiment, the temperature at which the uniform reaction mixture is agitated is greater than the boiling point of the solvent employed, and the pressure at which the uniform reaction mixture is agitated is greater than one atmosphere. In one embodiment, the temperature at which the uniform reaction mixture is agitated is greater than about 120° C. In an alternate embodiment, the temperature at which the uniform reaction mixture is agitated is greater than about 150° C. In yet another embodiment, the temperature at which the uniform reaction mixture is agitated is greater than about 180° C. In one embodiment, the temperature at which the uniform reaction mixture is agitated is in a range from about 180 to about 250° C., and in an alternate embodiment, in a range from about 210 to about 230° C. As the uniform reaction mixture is agitated water formed in the imidization reaction which occurs as the first reactant encounters the second reactant, is removed. Upon completion of imidization, reaction the uniform reaction mixture is deemed a uniform product mixture and comprises the product bisimide. In one embodiment, the imidization reaction is substantially complete when substantially all of the water formed in the imidization reaction has been removed from the uniform reaction mixture.

Of the various advantages presented by the method of the present invention, a significant advantage is that the reaction between the first reactant and the second reactant to form a product bisimide may be carried out at relatively high concentration. Higher concentrations result in correspondingly higher reaction rates, shorter reaction times, overall, improved efficiency, and higher concentrations of the product bisimide in the uniform product mixture. Thus, in one embodiment, the uniform product mixture comprises the product bisimide in an amount corresponding to at least 20 percent solids. As used herein, the term percent solids refers to the weight of the product bisimide relative to the weight of the solvent plus the weight of the product bisimide (i.e. % solids=(wt of product over wt product+wt of solvent)×100). In another embodiment, the product bisimide is present in the uniform product mixture in an amount corresponding to at least 25 percent solids. In yet another embodiment, the product bisimide is present in the uniform product mixture in an amount corresponding to at least 30 percent solids.

Various impurities are typically generated during the reaction of a diamine with an anhydride (or a dianhydride with a monoamine) to form a bisimide and appropriate steps for the removal of said impurities must be undertaken in applications sensitive to the presence of impurities. In general, minimization of the amounts of impurities present in the product bisimide is highly desirable. The method of the present invention provides product bisimides of high purity. In one embodiment, the uniform product mixture comprises less than about 1% by weight of a monoamine impurity, and preferably less than about 0.15% by weight of the monoamine impurity. As used herein, a monoamine impurity refers to a product comprising a free amine group or a protonated free amine group. In one embodiment, the product bisimide comprises as a monoamine impurity a mono-3-chorophthalimide of DDS, said mono-3-chorophthalimide of DDS comprising a free amine ($-NH_2$) group. In an alternate embodiment, the product bisimide comprises as a monoamine impurity a mono-4-chorophthalimide of DDS, said mono-4-chorophthalimide of DDS comprising a free protonated amine ($-NH_3^+$) group. In another embodiment, the product bisimide comprises a monoanhydride impurity, for example phthalic anhydride.

As noted, the method of the present invention is especially well suited to the preparation of relatively insoluble bisimides, for example the bis 3-chlorophthalimide of DDS. Because the method of the present invention provides for uniform reaction mixtures and uniform product mixtures, both the progress of the reaction and the reaction stoichiometry can be determined at any stage during the conversion of reactants to product, and thereafter as well. Solubilities of the product bisimides may be gauged the weight percent solubility of the product bisimide in a solvent at a particular temperature. As noted, in one embodiment, the product bisimide provided by the method of the present invention has a solubility in ortho-dichlorobenzene of less than about 10 percent by weight at a temperature of about 180° C.

In one embodiment, the method of the present invention further comprises verifying the stiochiometry of the first and second reactant in the uniform reaction mixture. The verification of the stiochiometry comprises withdrawing a sample of the uniform reaction mixture and analyzing the contents thereof. The phrase "analyzing the contents thereof" refers to any analysis process known in the art which permits the quantitative determination of the components of the uniform reaction mixture. Care must be exercised during withdrawal of the sample from the uniform reaction mixture because of the tendency of the uniform reaction mixture to become heterogeneous at temperatures and pressures below those at which the imidization reaction is conducted. In one embodiment, withdrawal of the sample from the uniform reaction mixture employs a heated tube linking (See element 44 in FIG. 1) the uniform reaction mixture to a heated sample port where samples are collected. In various embodiments, it has been discovered that the temperature at which the sampling tube is maintained is preferably high enough to maintain uniformity of the sample being withdrawn, and yet be at the same or slightly lower temperature than the uniform reaction mixture itself. Preferably, the sample is withdrawn as a homogeneous liquid. In one embodiment, the sample is withdrawn through a heated tube linking the uniform reaction mixture to a heated sample port, wherein said tube and sample port are maintained at a temperature in a range from about 180 to about 250° C. and at a pressure greater than about 1 atmosphere. In one embodiment, the heated sample port is connected to an evacuated sample bomb.

In one embodiment of the present invention, the method further comprises correcting the stoichiometry of the first and the second reactants. Stiochiometry corrections may be needed as a result of weighing errors and mechanical errors associated with the transfer of reactants into the reactor. The need for stoichiometric correction becomes evident when the analysis of a sample withdrawn from the uniform reaction mixture determines that the ratio of anhydride functionality to amine functionality is not within a required specification range, typically about 1.00-1.03 anhydride to amine ratio.

In certain embodiments of the present invention, the uniform reaction mixture may comprise a catalyst. Catalysts may in certain instances enhance the reaction rate of the first reactant with the second reactant to afford the product bisimide. In one embodiment, the method of the present invention employs as a catalyst a stable quaternary ammonium species such as hekaethylguanidinium bromide. In an alternate embodiment, the method of the present invention employs as a catalyst sodium phenyl phosphinate.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

EXAMPLES

The following examples are intended only to illustrate methods and embodiments in accordance with the invention, and as such should not be construed as imposing limitations upon the claims. Unless specified otherwise, all ingredients are commercially available from such common chemical suppliers as the Sigma-Aldrich Chemical Company.

Comparative Example 1

Stability of DDS/SPP Mixture at Elevated Temperatures

A 450 ml Parr pressure-rated reactor equipped with two side quartz windows was fitted with a partial condenser. The reator was charged with DDS (4,4'-diaminodiphenylsulfone) (14.898 g; 60 mmol), sodium phenylphosphinate (SPP) (50 mg; 0.3 mmol) and o-DCB (ortho-dichlorobenzene) (80 ml). The temperature was gradually raised to about 225-230° C. The mixture, observed through the quartz window, was observed to be transformed from an initially turbid mixture to a homogeneous solution as the temperature approached the melting point of DDS. The solution was maintained at about 230° C. for 1 hr. The mixture was then cooled to ambient temperature and analyzed. No significant change in the quality or purity of the recovered DDS was observed as analyzed using HPLC and $^1$H-NMR.

Comparative Example-2

Imidization in Parr Reactor with Up-Front ClPA Addition

A 450 ml Parr pressure-rated reactor equipped as in Comparative Example-1 with two side quartz windows and a partial condenser was charged with solid 3-chlorophthalic anhydride (3-ClPA, 21.578 g; 118.2 mmol), phthalic anhydride (0.2664 g; 1.8 mmol), DDS (14.898 g; 60 mmol), sodium phenylphosphinate (50 mg; 0.3 mmol) and o-DCB (85 ml). The reactor was sealed and the temperature was gradually raised. At about 180° C. the reaction mixture was observed to become homogeneous. As water of imidization was removed via the partial condenser the reaction gradually became heterogeneous and eventually the mixture became so thick that mixing of the solid adhering to the quartz window ceased to occur. As the temperature of the reaction mixture was raised further to about 190° C. the heterogeneous reaction mixture began to thin and the viscosity of the heterogeneous mixture was visibly diminished by the time the reaction mixture reached 200° C. Between about 210° C. and about 215° C. most of the solid material present in the reaction mixture dissolved. Thereafter the temperature was raised to 230° C. After about 7 hours imidization was deemed to be complete. Heating was discontinued and as the temperature decreased to about 215° C. the product bisimide began to precipitate from solution. When the temperature had decreased to about 200° C. the product mixture became so thick that efficient stirring could no longer be effected. This Comparative Example illustrates the limitations of "up-front" addition of all of the reactants. Thus, when each of the reactants is added to the reaction vessel at ambient temperature and thereafter the temperature of the reaction mixture is raised. While the reaction mixture is initially homogenous at about 180° C., as water of imidization is removed, the reaction mixture exhibits thick phase behavior which persists until the temperature reaches a higher threshold temperature, in this Comparative Example about 215° C., at which the reaction mixture becomes homogeneous again. The thick phase behavior is undesirable in that it prevents the efficient mixing of the reaction mixture while the thick phase persists and makes accurate measurement of reaction stoichiometry difficult.

Example-1

Imidization in Parr Reactor with Melt ClPA Addition—Procedure:

A 450 ml Parr pressure-rated reactor equipped as in Comparative Example-1 was charged with DDS (14.898 g; 60 mmol), sodium phenylphosphinate (50 mg, 0.3 mmole) and o-DCB (85 mL). The temperature was gradually raised to about 225-230° C. The resultant homogeneous solution was maintained at about 230° C. for 1 hr after which time molten 3-chlorophthalic anhydride (3-ClPA, 21.578 g, 118.2 mmole) and phthalic anhydride (0.2664 g; 1.8 mmol) at about 130° C. was added from a stainless steel bomb mounted on top of the reactor. The addition of 3-ClPA was carried out over a period of about 30 to 40 minutes. Water of imidization was azeotropically removed from the reactor via the partial condenser. Throughout the 3-ClPA/PA addition, and thereafter, the reaction mixture was observed to remain a homogeneous solution while at 230° C. No thick phase behavior was observed during the reaction. As the reactor was cooled, the product bisimide was observed to precipitate over a temperature range from about 215 to about 210° C. The reactor was vented when the temperature had decreased to about 170° C. and a sample of the pasty product mixture was withdrawn and analyzed by HPLC. The quality of the product bisimide ("ClPAMI") was found to be equivalent to the quality of ClPAMI made using known methods.

Larger scale imidization reactions using the method of the present invention were conducted in a 5 gallon reactor. The larger reactor was equipped with sampling features which allowed the withdrawal of samples of the reaction mixture as a homogeneous solution without venting the reactor or causing the product bisimide to precipitate during sampling. Examples 2 and 3 are illustrative.

Figure 1:
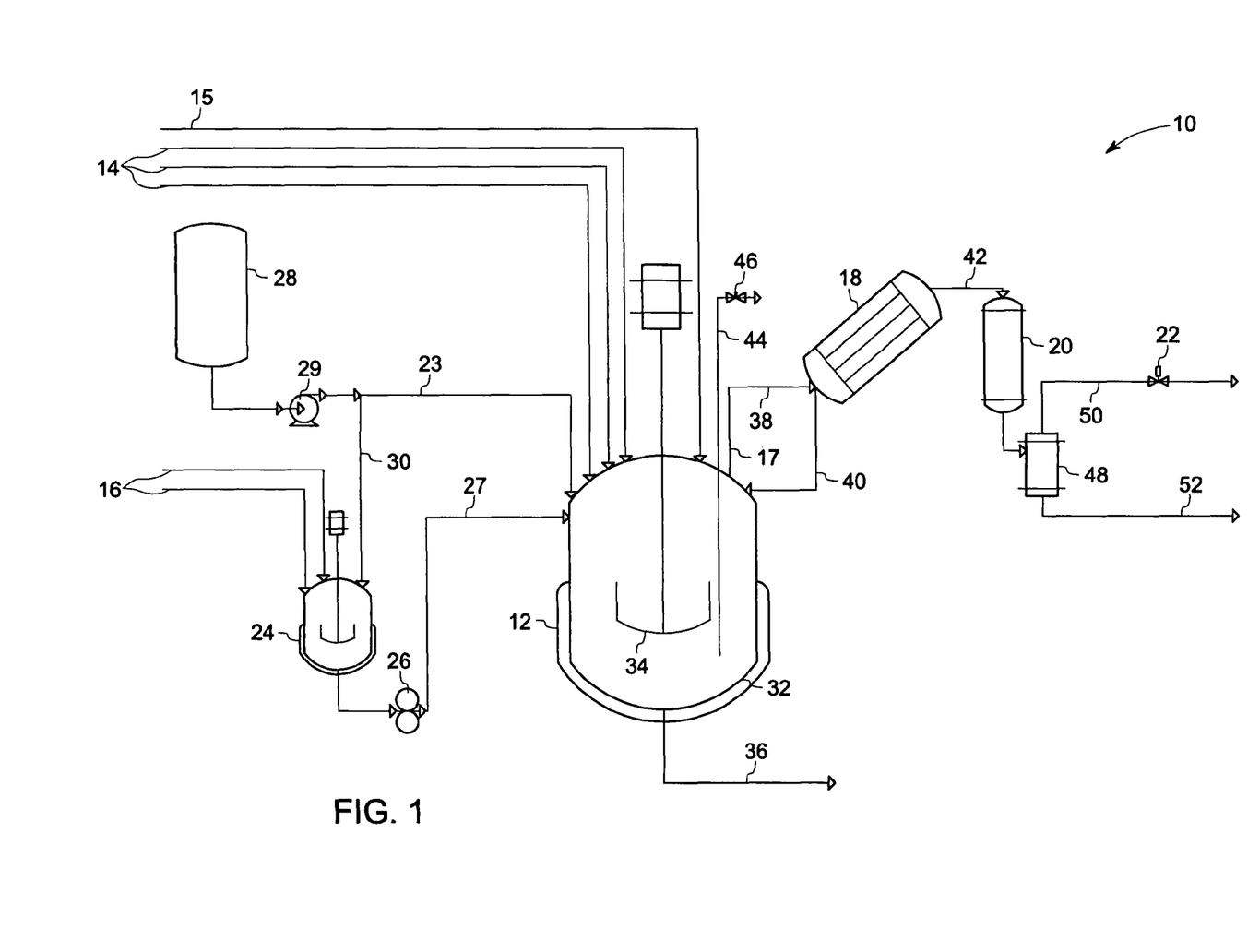
FIG. 1 is a schematic representation of a reactor set up which may be used for carrying out the method of the present invention.

A reactor system 10 utilized in various embodiments of the invention is shown in FIG. 1. The reactor system comprised a 5-gallon stainless steel reactor 12 connected directly to monomer and catalyst feed lines 14 and inert gas purge line 15, and indirectly to feed lines 16 for addition of molten reactants. The reactor 12 was connected via distillation line 17 to a partial reflux condenser 18, a total condenser 20 and a back-pressure regulator 22. Feed lines 14 were employed for the batchwise addition of DDS, SSP catalyst, and optionally a portion of the ClPA, whereas, monomer feed lines 16 served for the semi-batch mode introduction of a molten mixture of ClPA and the chain stopper phthalic anhydride (PA). Solvent could be introduced into the reactor via solvent feed line 23.

Reactant DDS, ODCB solvent and SPP catalyst were charged to the reactor 12 in batch mode, i.e. prior to starting the reaction. In some reactions a portion of the ClPA was added directly to the reactor 12 via feed lines 14 prior to heating the reaction mixture. In some reactions, all of the ClPA and PA was added as a melt. Thus ClPA and PA were combined in heated tank 24 and heated to form a melt which was transferred through melt feed pump 26 and melt feed line 27 into reactor 12 at the desired rate and reactor conditions. To insure quantitative transfer of the molten reactants from heated tank 24, o-DCB solvent from solvent feed tank 28 was transferred via solvent pump 29 through flush line 30 to rinse the interior surfaces of heated tank 24, melt feed pump 26, and melt feed line 27 and the rinse solvent was transferred into reactor 12.

The reactor 12 was heated with a hot oil jacket 32 and stirred by an agitator 34 equipped with one or two pitched blade impellers, each with 4 blades. Agitation rates were varied from 100-250 RPM, corresponding to a power to volume ration range of 0.15-2.5 kW/m$^3$. The reactor was also equipped with an appropriately valved reactor drain line 36 for recovery of product bisimide.

Reactor overhead vapors 38 contained ODCB solvent and water of imidization. The partial reflux condenser 18 efficiently condensed ODCB solvent vapor and returned condensed ODCB to the reactor via solvent return 40. Because the partial reflux condenser was operated at a temperature lower than the boiling point of ODCB but higher than the boiling point of water, the partial condenser overhead stream 42 emerging from the partial reflux condenser was highly enriched in water vapor. Overhead stream 42 contained some ODCB, however due to the formation of the ODCB/water azeotrope. The partial condenser, 18, is useful in minimizing the loss of ODCB solvent to the amount that is azeotropic, thus avoiding the need to add back solvent in order to maintain the desired solids concentration in the reactor. The solids concentration controls the solubility of the components as well as the reaction kinetics. The vapor flow rate and partial condenser temperature dictated how much ODCB was allowed overhead, but generally the minimum boiling azeotrope comprised about 1:1 water to ODCB by volume. The total condenser 20 was used to condense overhead stream 42 for recovery and recycle of the ODCB.

The backpressure regulator 22 was used to control the reactor pressure to maintain reaction temperatures above the normal boiling point of the ODCB solvent. The pressures employed spanned a range from about 1 to about 40 psig of backpressure, with a typical range of from about 18 to about 35 psig corresponding to temperatures in a range from about 220 to about 235° C.

Sampling was done through a heated sampling line 44 through which samples of the contents of the reactor were taken. The sampling line 44 was heated to a temperature at which the sample of the reaction mixture remained a homogeneous liquid during sampling. Samples were transferred through a heated sample port 46 into an evacuated sample bomb (not shown). In order to minimize later sampling errors, the sampling line was cleaned after each sample removal by flushing with solvent in the direction of the reactor.

Analysis during the imidization reaction provided an opportunity to correct stoichiometric imbalances brought about by weighing or transferring errors of the reactants to the reactor. Stoichiometric correction was deemed necessary when analysis determined that the ratio of anhydride functionality to amine functionality fell outside of a specified range, typically a ratio of anhydride to amine in a range from about 1.00 to about 1.03. For small stoichiometric corrections diamine or anhydride could be added as a slurry in ODCB through heated sample port 46 using a driving pressure greater than the internal pressure of the reactor. For larger stoichiometric corrections molten diamine or anhydride was added followed by a solvent flush.

Reactor 12 was also equipped a condensate holding tank 48 downstream of total condenser 20, vent line 50 in gaseous communication with back pressure regulator 22, and condensate drain line 52.

Example 2

The 5-gallon reactor described above and shown in FIG. 1 was equipped with 2 flights of 4-blade pitched turbines, and was charged according to Table I below.

TABLE I

| Component | Mass (g) | Moles | Source |
| --- | --- | --- | --- |
| 4,4 Diamino Diphenyl Sulfone (DDS) | 1520.8 | 6.125 | Atul |
| Phthalic Anhydride (PA) | 27.19 | 0.184 | Aldrich |
| Sodium Phenyl Phosphinate (SPP) | 5.0 | 0.030 | Akzo |
| 3-Chloro Phthalic Anhydride (ClPA) | 2202.8 | 12.066 | Pressure Chem. |
| 1,2 Dicholoro Benzene (ODCB) | 9756 | 66.37 | PPG Grade F |

The reactor was purged with inert gas at 100 SCCM, and the agitation rate was set to 200 rpm. The partial condenser was heated by means of an oil jacket to a temperature of about 130° C. The reactor was heated by setting the reactor oil jacket temperature to 200° C. After 30-minutes of heating, the reactor oil jacket temperature was increased to 230° C. The reactor internal temperature reached a temperature of about 177° C. Water and ODCB were collected as condensed distillate. The reactor pressure was 26.3 psig. Amounts of distillate collected of the course of the reaction, reactor temperature and pressure are shown-in Table II.

TABLE II

| Time (min) | Reactor T (° C.) | Reactor P (PSIG) | $H_2O$ (ml) | ODCB (ml) |
| --- | --- | --- | --- | --- |
| 3 | 184.1 | 26.3 | 36 | 25 |
| 6 | 190.4 | 26.3 | 86 | 52 |
| 8 | 197.4 | 26.0 | 114 | 76 |
| 10 | 205.9 | 26.4 | 132 | 92 |
| 16 | 219.2 | 25.0 | 171 | 117 |
| 22 | 223.5 | 26.4 | 186 | 128 |
| 26 | 225.6 | 26.4 | 191 | 134 |
| 30 | 226.7 | 26.3 | 194 | 138 |
| 35 | 227.7 | 26.3 | 198 | 140 |
| 57 | 230.7 | 26.2 | 207 | 145 |

After about 1.4 hrs of distillation, the reaction mixture was sampled via the heated sampling port. HPLC analysis of the homogeneous sample indicated that additional 3-ClPA (6.1 grams) was needed to adjust the stoichiometry to within the specified limits. At 2.5 hours of distillation, the 6.1 grams of 3-ClPA was added as a solution of about 9.8 wt % in ODCB.

After a total of 4.5 hours the reaction mixture was again sampled. Sample analysis by HPLC indicated that ratio of anhydride to amine was in the range required, from about 1.00 to about 1.03. Therefore, there was no need for any further stoichiometry correction. Heating was continued for a total 9.5 hours at a reactor oil jacket set temperature of 230° C. The reaction was then cooled and diluted with ODCB to provide a slurry of the product so that approximately 3500 grams of solids was obtained as a slurry in 17.8 Kg of ODCB.

Example 3

Melt 3-CLPA Semi-Batch Reaction Mode

The 5-gallon reactor described above and shown in FIG. 1 was equipped with 2 flights of 4-blade pitched turbines, and was charged according to Table III below.

TABLE III

| Component | Mass (g) | Moles | Source |
| --- | --- | --- | --- |
| 4,4 Diamino Diphenyl Sulfone (DDS) | 1520.8 | 6.125 | Atul Inc. |
| Sodium Phenyl Phosphinate (SPP) | 5.0 | 0.030 | Akzo Inc. |
| 1,2-Dicholoro Benzene (ODCB) | 9991 | 68.0 | PPG Grade F |

Heated tank 24 (FIG. 1) was charged with phthalic anhydride (PA) and 3-chlorophthalic anhydride (3-ClP) in the amounts shown in Table IV and heated to 140° C. in order to melt the 3-ClPA/PA solids. ODCB (240 grams) was then added to the molten mixture of 3-ClPA and PA which was completely miscible with the ODCB. Thus, the mixture in heated tank 24 comprised 3-ClPA (89.2 wt %), ODCB (9.7 wt %), and PA (1.1 wt %). The small amount of ODCB solvent employed helped to facilitate complete transfer of the anhydride reactants into the reaction mixture.

TABLE IV

| Component | Mass (g) | Moles | Source |
|---|---|---|---|
| Phthalic Anhydride | 27.20 | 0.184 | Aldrich |
| 3-Chlorophthalic Anhydride | 2203.0 | 12.067 | Pressure Chem. |
| 1,2-Dicholorobenzene | 240.0 | 1.63 | PPG Grade F |

The 5-gallon reactor was purged with inert gas at 100 SCCM, and the agitation rate was set to 200 rpm. The partial condenser was heated by means of an oil jacket to a temperature of 130° C. The reactor was heated commenced by setting the reactor oil jacket temperature to 180° C. After 30-minutes, the oil jacket temperature was increased to 225° C. At the 1.0-hour mark, the reactor reached a temperature of 226° C., at which point the melt addition of the 3-ClPA-PA-ODCB melt mixture from heated tank 24 was commenced. The reactor pressure was 25.1 PSIG. The 3-ClPA-PA-ODCB melt mixture was pumped via melt feed pump 26 and melt feed line 27 into reactor 12 at an average rate of about 21.5 grams/minute. Addition of the 3-ClPA at a temperature in excess of 210° C. avoided the thick phase reaction stage observed when the reactants are brought into contact at temperatures below about 190° C.

About 15 minutes after the addition of the 3-ClPA-PA-ODCB melt mixture was initiated, water and ODCB distillate were observed in the overheads from the partial reflux condenser 18. Addition of the 3-ClPA-PA-ODCB melt mixture required about 2 hours to complete. During the addition of the 3-ClPA-PA-ODCB melt mixture, the amounts of water and ODCB condensed from the overheads emerging from the partial reflux condenser were recorded as a function of time and are recorded in Table V, along with the reactor temperature and pressure profiles.

TABLE V

| Time (min)* | Reactor T (° C.) | Reactor P (PSIG) | H$_2$O (ml) | ODCB (ml) |
|---|---|---|---|---|
| 10 | 222.4 | 26.5 | 23 | 20 |
| 20 | 223.1 | 26.4 | 42 | 33 |
| 25 | 223.2 | 26.4 | 53 | 39 |
| 30 | 223.3 | 26.5 | 63 | 46 |
| 35 | 223.5 | 26.5 | 75 | 52 |
| 40 | 223.7 | 26.4 | 84 | 60 |
| 45 | 223.7 | 26.5 | 94 | 67 |
| 50 | 223.8 | 26.5 | 102 | 76 |
| 55 | 223.8 | 26.5 | 111 | 83 |
| 60 | 223.8 | 26.5 | 121 | 90 |
| 65 | 223.8 | 26.6 | 131 | 97 |
| 70 | 224.1 | 26.6 | 137 | 107 |
| 75 | 224.2 | 26.5 | 147 | 117 |
| 80 | 224.3 | 26.5 | 153 | 123 |
| 85 | 224.5 | 26.3 | 161 | 131 |
| 90 | 224.8 | 26.3 | 169 | 137 |
| 95 | 224.8 | 26.3 | 176 | 141 |
| 98 | 225.1 | 26.3 | 180 | 145 |
| 115 | 227.4 | 26.4 | 194 | 156 |
| 145 | 230.2 | 26.5 | 203 | 163 |

*Time is referenced from the first observation of water and ODCB in the overheads from the partial reflux condenser.

Upon completion of the addition of the 3-ClPA-PA-ODCB melt mixture, heated tank 24 was rinsed with about 525 grams of ODCB, and the rinse was added through melt feed pump 26 and melt feed line 27 into reactor 12. The reactor temperature was maintained at 230° C. After 3.2 hours of reaction time, a homogeneous sample of the reaction mixture was taken. The analysis indicated that approximately 9 grams of DDS was needed to bring the reaction stoichiometry to within the specification. The needed DDS (9 grams) was added to the reactor at about 4.5 hours of total reaction time as a 20 wt % slurry of DDS in ODCB. Following the DDS addition the reaction was continued for an additional 7 hours to assure complete imidization of all amine groups present. The total reaction time was 11.5 hours. The reaction mixture was then allowed to cool and was diluted with ODCB to afford a product mixture as a slurry comprising approximately 3500 grams of product bisimide in about 17.2 kilograms (Kg) of ODCB.

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. A method for making a bisimide, the method comprising:
   (a) adding a molten first reactant to a mixture comprising a solvent having a boiling point greater than 120° degrees Celsius at 1 atmosphere and a second reactant to provide a uniform reaction mixture wherein said first reactant is an anhydride and said second reactant is a diaminodiphenylsulfone;
   (b) agitating the uniform reaction mixture while removing water formed in an imidization reaction to afford a uniform product mixture comprising a product bisimide, the product bisimide being present in an amount corresponding to at least 20 percent solids, the product bisimide having a solubility in ortho-dichlorobenzene of less than about 10 percent by weight at a temperature of about 180° C.;
   said adding and said agitating being carried out at a temperature of 210-230° C.,
   wherein the dianhydride comprises a haloaromatic anhydride, a phthalic anhydride, a nitrophthalic anhydride, 4-cyanophthalic anhydride, or a dianhydride of structure (VI)

wherein R$^1$ is a halogen atom, a nitro group, a C$_1$- C$_{12}$ aliphatic radical, C$_3$-C$_{12}$ cycloaliphatic radical, or a C$_3$-C$_{12}$ aromatic radical; b is independently at each occurrence 0 or an integer from 1 to 3; and W is a bond, an oxygen atom, a sulfur atom, a sulfinyl group, a sulfonyl group, a selenium atom, a hexafluoroisopropylidene group, a C$_1$- C$_{30}$ aliphatic radical, a C$_3$-C$_{30}$ cycloaliphatic radical, or a C$_3$- C$_{30}$ aromatic radical, or a carbonyl group.

2. The method according to claim 1, wherein the solvent is selected from the group consisting of ortho-dichlorobenzene, para-dichlorobenzene, chlorobenzene, dichlorotoluene, 1,2,4-trichlorobenzene, diphenyl sulfone, phenetole, anisole, veratrole, toluene, xylene, mesitylene, o-cresol, and mixtures thereof.

3. The method according to claim 1, wherein the solvent is ortho-dichlorobenzene.

4. The method according to claim 1, wherein the first reactant is a haloaromatic anhydride.

5. The method according to claim 4, wherein the haloaromatic anhydride is selected from the group consisting of 3-ClPA, 4-ClPA, and mixtures thereof.

6. The method according to claim 1, wherein the uniform product mixture comprises less than about 0.15% by weight of a monoamine impurity.

7. The method according to claim 1, wherein said first reactant comprises phthalic anhydride.

8. The method according to claim 1, wherein the product bisimide has a solubility in ortho-dichlorobenzene of less than 5 percent by weight at a temperature of about 180° C.

9. The method according to claim 1, wherein the first reactant is used in a stoichiometric excess of about 0.3 percent.

10. The method according to claim 1, further comprising verifying the stoichiometry of the reaction mixture.

11. The method according to claim 10, further comprising introducing additional first reactant or additional second reactant in response to a stoichiometry verification step.

12. A method for making a bisimide, the method comprising:
  (a) adding molten chlorophthalic anhydride to a mixture comprising ortho-dichlorobenzene and 4,4'-diaminodiphenylsulfone to provide a uniform reaction mixture wherein the mixture is at a temperature greater than 210° C.;
  (b) agitating the uniform reaction mixture while removing water formed in an imidization reaction to afford a uniform product mixture comprising a product bisimide, the product bisimide being present in an amount corresponding to at least 20 percent solids, the product bisimide having a solubility in ortho-dichlorobenzene of less than about 10 percent by weight at a temperature of about 180° C.;
  said agitating being carried out at a temperature greater than the boiling point of the ortho-dichlorobenzene at a pressure greater than 1 atmosphere.

* * * * *

UNITED STATES PATENT AND TRADEMARK OFFICE
CERTIFICATE OF CORRECTION

PATENT NO.       : 7,981,996 B2                                Page 1 of 1
APPLICATION NO.  : 11/600538
DATED            : July 19, 2011
INVENTOR(S)      : Farid Fouad Khouri and Albert Santo Stella It is certified that error appears in the above-identified patent and that said Letters Patent is hereby corrected as shown below:

In the Claims

In column 20, line 47, delete "dianhydride" and insert --anhydride-- therefor.

Signed and Sealed this
Eighth Day of September, 2015

Michelle K. Lee
*Director of the United States Patent and Trademark Office*